United States Patent

Weismann

[11] Patent Number: 5,876,352
[45] Date of Patent: Mar. 2, 1999

[54] PROCESS FOR DETERMINING THE MECHANICAL PROPERTIES OF THE RESPIRATORY SYSTEM OF A RESPIRATED PATIENT AND DEVICE FOR CARRYING OUT THE PROCESS

[75] Inventor: Dieter Weismann, Grönau, Germany

[73] Assignee: Drägerwerk AG, Lübeck, Germany

[21] Appl. No.: 975,334

[22] Filed: Nov. 20, 1997

[30] Foreign Application Priority Data

May 17, 1997 [DE] Germany .................. 197 20 882.7

[51] Int. Cl.⁶ ........................................ A61N 5/00
[52] U.S. Cl. ............................ 600/529; 600/538
[58] Field of Search ............................ 600/529, 532, 600/533, 538, 539, 541, 542, 540

[56] References Cited

U.S. PATENT DOCUMENTS

| | | | |
|---|---|---|---|
| 5,233,998 | 8/1993 | Chowienczyk et al. | 600/533 |
| 5,261,397 | 11/1993 | Grustein | 600/533 |
| 5,316,009 | 5/1994 | Yamada | 600/538 |
| 5,584,300 | 12/1996 | Gaides | 600/532 |

FOREIGN PATENT DOCUMENTS 0 521 515 A1  1/1993  European Pat. Off. .

OTHER PUBLICATIONS

Kreit et al. 1994 "Patient Work of Breathing during Pressure Support . . . " *American Journal of Respiratory and Critical Care Medicine.*

Drägerwerk Jul. 1994 EVITA 4, Intensive Care Ventilator *EVITA User's Manual.*

Sydow et al. 1991 "Improved determination of static . . . " *Intensive Care Medicine.*

Matamis et al. 1984 "Total Respiratory Pressure–Volume Curves . . . " *Chest.*

*Primary Examiner*—Robert L. Nasser
*Assistant Examiner*—Michael Astorino
*Attorney, Agent, or Firm*—McGlew and Tuttle, P.C.

[57] ABSTRACT

A process and device for determining mechanical properties of a respiratory system of a patient connected to a respirator, wherein a short-term occlusion of the patient's airways is performed during an inspiration phase and/or an expiration phase. Initiating of the occlusion is at different points in time within the breathing cycle and during a plurality of breaths. The respiratory flow and the inhaled or exhaled volume of the patient is determined at the beginning of this occlusion. The airway pressure is also measured during this occlusion. The change occurring over time in the airway pressure during a measurement time falling within the occlusion time is determined. Also determined is the course over time of the change occurring over time of the muscle pressure of the patient from the measured values. The course over time of the muscle pressure is calculated by integrating this course over time.

18 Claims, 7 Drawing Sheets

PROCESS FOR DETERMINING THE MECHANICAL PROPERTIES OF THE RESPIRATORY SYSTEM OF A RESPIRATED PATIENT AND DEVICE FOR CARRYING OUT THE PROCESS

FIELD OF THE INVENTION

The present invention pertains to a process for determining the mechanical properties of the respiratory system of a patient connected to a respirator, wherein the patient's airways are briefly occluded during a phase of inspiration and/or a phase of expiration, and the respiratory flow and the patient's inhaled and exhaled tidal volume are determined at the beginning of this occlusion, and the pressure in the airways is measured during this occlusion, as well as to a device for carrying out this process.

BACKGROUND OF THE INVENTION

The determination of the mechanical properties of the respiratory system of a patient whose respiration is assisted by means of a respirator, which properties are characterized by the values of the compliance C and the resistance R as well as by an indicator of the activity of the respiratory muscles, remains an unsolved problem if the patient's spontaneous breathing is not negligible.

The so-called Super-Syringe process was described in the scientific literature (D. Matamis et al., Chest, 86, 1: 58 (1984)) for relaxed patients. The patient is separated from the respirator and the patient's lungs are slowly expanded by pressing in gas by means of a syringe. The airway pressure and the tidal volume pressed into the lungs are thus measured simultaneously. Thus, this process furnishes the pressure-volume relationship of the respiratory system under quasi-static conditions.

The drawback of this process is the long time needed for the measurement, during which the measured values may be distorted by the gas exchange occurring simultaneously. Furthermore, the patient must be separated from the respirator, which leads to a disturbance in respiration. The process is complicated and requires separate sensors for pressure and volume, and it is therefore used for scientific purposes only. This process cannot be used, in principle, in spontaneously breathing patients.

Sydow et al. (*Intensive Care Med.* (1991), 17: 108) describe a process in which the respiration is interrupted at a predetermined point by means of rapidly switching valves (this procedure is called occlusion). After pressure equalization, the pressure present in the lungs in measured. The interruption is performed one after another during a plurality of breaths, and a waiting time, during which the lungs can again assume their initial state, is inserted between the individual interruptions.

This process fails when the patient is not relaxed. A determination of the mechanical properties of the respiratory system is thus impossible in the presence of spontaneous breathing.

Furthermore, a process has been known for the determination of the respiration drive, in which the inspiration valve is closed before the beginning of a spontaneous inspiration (EVITA User's Manual, Drägerwerk, Lübeck, e.g., GA EVITA 4, July 1994 edition, p. 127). The pressure drop during the first 100 msec of the inspiration, the so-called PO.1, is evaluated as an indicator of the respiration drive. However, this process does not make it possible to determine the spontaneous breathing during the entire cycle. Furthermore, it does not make it possible to determine the mechanical properties of the respiratory system.

Kreit et al. (*Am. J. Respir. Care Med.*(1994), 149: 1085) described a mathematical method for the analysis of spontaneous breathing during assisted respiration, wherein the force of the respiratory muscles is represented by the so-called muscle pressure $P_{mus}$. If the compliance C and the resistance R are known, the muscle pressure $P_{mus}$ can be calculated by means of the known mathematical relationship between the respiration pressure $P_{aw}$, the muscle pressure $P_{mus}$, the tidal volume V and the respiratory flow dV/dt:

$$P_{mus}+P_{aw}=R^* \, dV/dt+V/C \qquad (1)$$

$$P_{mus}=R^* \, dV/dt+V/C-P_{aw} \qquad (1a)$$

Three of the six factors of this equation can be measured ($P_{aw}$, dV/dt and V). The authors assume the mechanical properties (compliance and resistance) of the respiratory system to be known by using for them values which had been measured before the beginning of the spontaneous breathing. This makes it possible to calculate $P_{mus}$.

The drawback of this process is that its use requires the knowledge of R and C, but these variables can be determined only in the absence of spontaneous breathing. Changes in the mechanical properties of the respiratory system, which usually occur during respiration, thus inherently lead to errors in the determination of $P_{mus}$. Furthermore, as is apparent from Equation (1a), $P_{mus}$ is determined by subtracting relatively high values. Thus, small errors in measurement thus lead to a relatively great error in the determination of $P_{mus}$.

A device for monitoring the activity of the respiratory muscles of a respirated patient is described in EP 521 515. The muscle pressure $P_{mus}$ is calculated from the measured values of the respiration pressure $P_{aw}$ and the respiratory flow dV/dt according to the following formula:

$$P_{mus}=-P_{aw}+R^* \, dV/dt+E^*$$

$$P_{mus} = -P_{aw} + R^* \, dV/dt = E \, * \, \int(dV/dt)dt \qquad (2)$$

with the elastance E=1/C.

This device also has the drawback that the values of resistance and compliance (or elastance) must be known. To measure these values, the patient's spontaneous breathing must be suppressed by temporarily paralyzing the respiratory muscles.

These prior-art processes and devices have the drawback that the patient's spontaneous breathing must be massively disturbed to determine the mechanical properties of the respiratory system of a patient.

SUMMARY AND OBJECTS OF THE INVENTION

The object of the present invention is to provide a process and a device for carrying out this process, which shall make it possible to determine the mechanical properties of compliance, resistance and muscle pressure of the respiratory system of a respirated patient in all respiration processes. The normal breathing shall be disturbed only minimally; in particular, interruption of the spontaneous breathing shall not be necessary. The use of additional sensors or valves shall not be compulsorily necessary.

This object is accomplished by determining the changes over time in the airway pressure during a measurement time falling within the occlusion time; by initiating the occlusion during a plurality of breaths at different points in time within the breathing cycle; by determining the course over time of the change occurring over time in the patient's muscle pressure from the measured values; and by calculating the course of the muscle pressure over time by integrating this course over time.

The advantage of the present invention is that a continuous measurement of the patient's muscle pressure and thus a monitoring of the intensity of his spontaneous breathing is possible without first determining the compliance and the resistance and without the suppression of the patient's spontaneous breathing, which is associated with the prior art. Changes in the compliance and the resistance of the patient's lungs are detected continuously.

An occlusion is brought about for a short time at determinable points during a breathing cycle by controlling the respirator, during which the respiration or spontaneous breathing of the patient is interrupted by closing an inspiration valve and an expiration valve of the respirator or by closing a special occlusion valve at a patient connection. The occlusion may be triggered by the reaching of a presettable time since the beginning of the inspiration, by the reaching of a presettable volume or by the reaching of a presettable respiratory flow.

A waiting time of about 20 to 200 msec, during which vibrations in the respiratory system subside, is inserted after the beginning of the occlusion. If an occlusion valve is used at the patient connection, only a short waiting time is needed, because the length of the vibrating system is very short. The pressure and the changes over time in the pressure are measured after this waiting time during a measurement time of about 50 to 200 msec. The volume inhaled and exhaled at the beginning of the occlusion and the respiratory flow at the beginning of the occlusion are determined as well. The end of the measurement time must be selected to be such that the patient will not yet have responded to the occlusion with a change in his muscular tone.

The respiratory flow is equal to zero after the beginning of the occlusion. Consequently, $$P_{mus} + P_{aw} = V/C \text{ and} \qquad (3)$$

$$dP_{mus}/dt = -dP_{aw}/dt. \qquad (4)$$

By measuring the slope of the change in pressure during the measurement time, it is thus possible to obtain a value for the change occurring over time in the muscular tone $dP_{mus}/dt$ for a defined point in time within the breathing cycle (the value may be associated, e.g., with the middle of the measurement time). If the occlusion and the determination of $dP_{mus}/dt$ are performed during a plurality of breaths at different points in time within the breathing cycles, the course over time of $dP_{mus}/dt$ over the breathing cycle is obtained.

The integration of the course over time of $dP_{mus}/dt$ according to one of the known mathematical methods will then furnish—with the exception of an arbitrary additive constant K—the course over time of the muscular tone $P_{mus}(t)$:

$$P_{mus}(t) = -\int (dP_{mus}/dt + K \qquad (5)$$

By adding up the measured airway pressure $P_{aw}$ and the calculated muscle pressure Pmus to a total pressure $P_{tot}$, we obtain:

$$P_{tot} = P_{aw} + P_{mus} = v/c + K'. \qquad (6)$$

By plotting $P_{tot}$ over the volume V, a straight line is obtained, whose slope represents the elastance E=1/C of the respiratory system.

The value for the resistance R of the patient's lungs is calculated from the difference of the airway pressures immediately before ($P_{aw0}$) and immediately after ($P_{awr}$) the occlusion, divided by the respiratory flow immediately before the occlusion taking place at the time $t_0$:

$$R = (P_{aw0} - P_{awr})/(dV/dt) (t_0) \qquad (7)$$

The value $P_{awr}$ is obtained by re-extrapolating $t_o$ the point in time to by means of a straight line $P_{aw}$ fitted to the measured values of the change in $P_{aw}$ during the measurement time.

If the volume is measured with an internal sensor of the respirator, it is useful to correct the measured volume by the effect of the compliance of the respiratory system to increase the accuracy of the process.

Now, $$V_{patient} = V - C_{sys} * \Delta P \qquad (8)$$

in which $\Delta P$=pressure difference between the beginning of the inspiration and the point in time at which the measurement is performed, and $C_{SYS}$=compliance of the respiratory system.

The above calculations will then be performed with the corrected value of $V_{patient}$ instead of with the value V. This correction is not necessary in the case of the measurement of the volume with a sensor arranged at a patient connection, i.e., in the immediate vicinity of the patient's s mouth.

The determination of the values of C, R, and $P_{mus}$ may also be performed with modified equations, in which the terms are treated as variables of the volumes rather than as variables of the time.

The prerequisite for an accurate determination of the values of C, R, and $P_{mus}$ is that all the breaths used for the integration of $dP_{mus}/dt$ shall be extensively identical. This is ensured by checking the agreement of the courses over time of the pressure, respiratory flow and volume before the beginning of the occlusion for all breaths. To do so, the courses are recorded during a reference breath, and the corresponding values of the current breath are compared with this reference breath. If the deviations are below a limit value, the breath is used for the evaluation. Depending on the requirements on accuracy, a value of 5% to 25% of the corresponding measured value is selected as the limit value.

It is also possible to record a plurality of reference breaths, to treat the values associated with the corresponding reference breaths separately during the evaluation, and to average the end results. This makes it possible to use more breaths for the evaluation.

The sensors for measuring the volume and the airway pressure may be arranged directly at the patient connection, or the sensors already present in a respirator may be used.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENT

Figure 1:
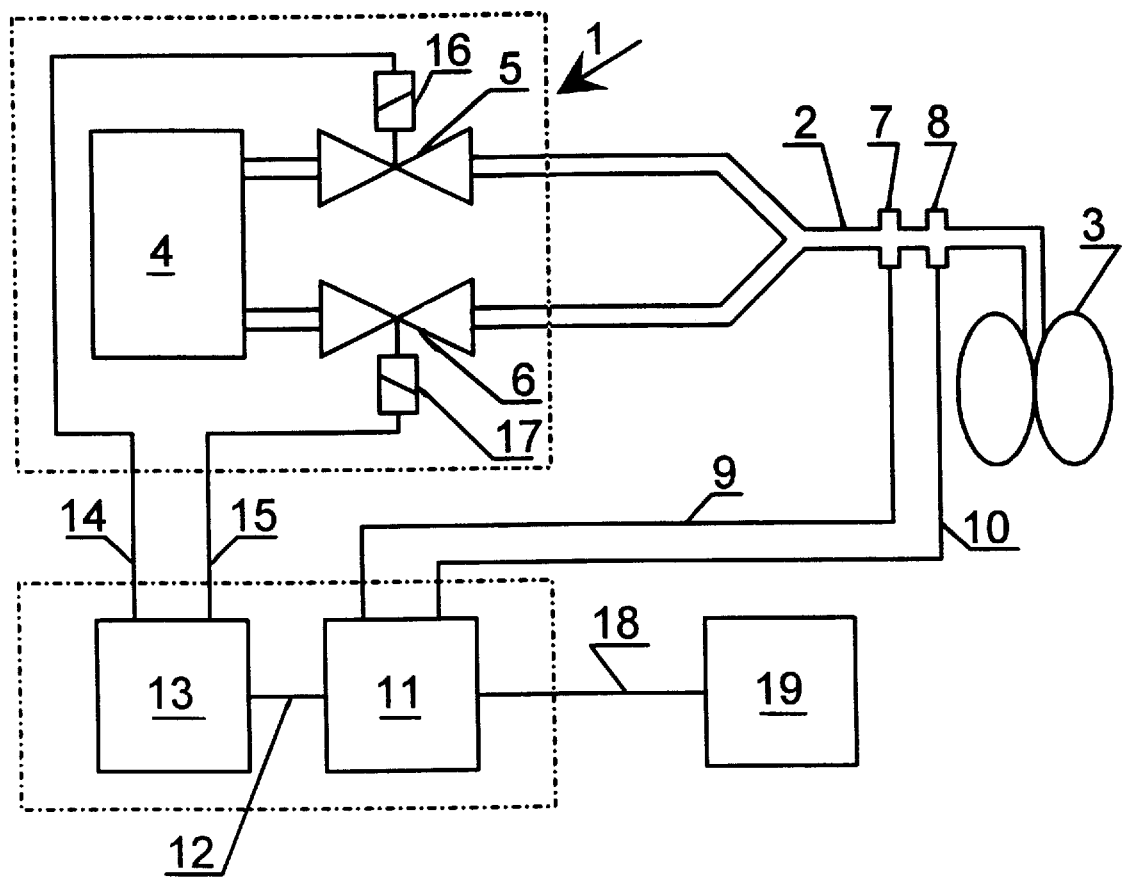
FIG. 1 shows a respirator with a patient connected thereto.

The respirator 1 shown in FIG. 1 is connected via a patient connection 2 to a patient 3 (whose respiratory organs only are represented symbolically). A respiration control unit 4, which is not described more specifically and is connected to the patient connection 2 via an inspiration valve 5 and an expiration valve 6, is arranged in the respirator 1. A flow sensor 7 and a pressure sensor 8 are arranged in the patient connection 2. The sensors are connected via measuring lines 9 and 10 to an evaluating unit 11, which in turn is connected to a control unit 13 via a line 12. The control unit 13 is connected via control lines 14 and 15 to actuators 16 and 17 for actuating the inspiration valve 5 and the expiration valve 6. The evaluating unit 11 is connected to an output device 19 via an output line 18.

While the patient 3 is being respirated by the respirator 1, the values measured with the sensors 7 and 8 are evaluated by means of the evaluating unit 11. If the course of a breath corresponds to the course of a reference breath stored before within set limits, the control unit 13 initiates an occlusion at a defined point in time within the breath. To do so, the inspiration valve 5 and the expiration valve 6 are closed by actuating the actuators 16 and 17. The occlusion is initiated at different times within the respective breath during a plurality of breaths. The evaluating unit 11 determines the variables of compliance and resistance of the patient's lungs as well as the course of the muscle pressure from the measured values, and it sends these variables to the output device 19 via the output line 18. The output device 19 may be a display unit, e.g., a monitor, on which the variables are represented graphically.

Figure 2:
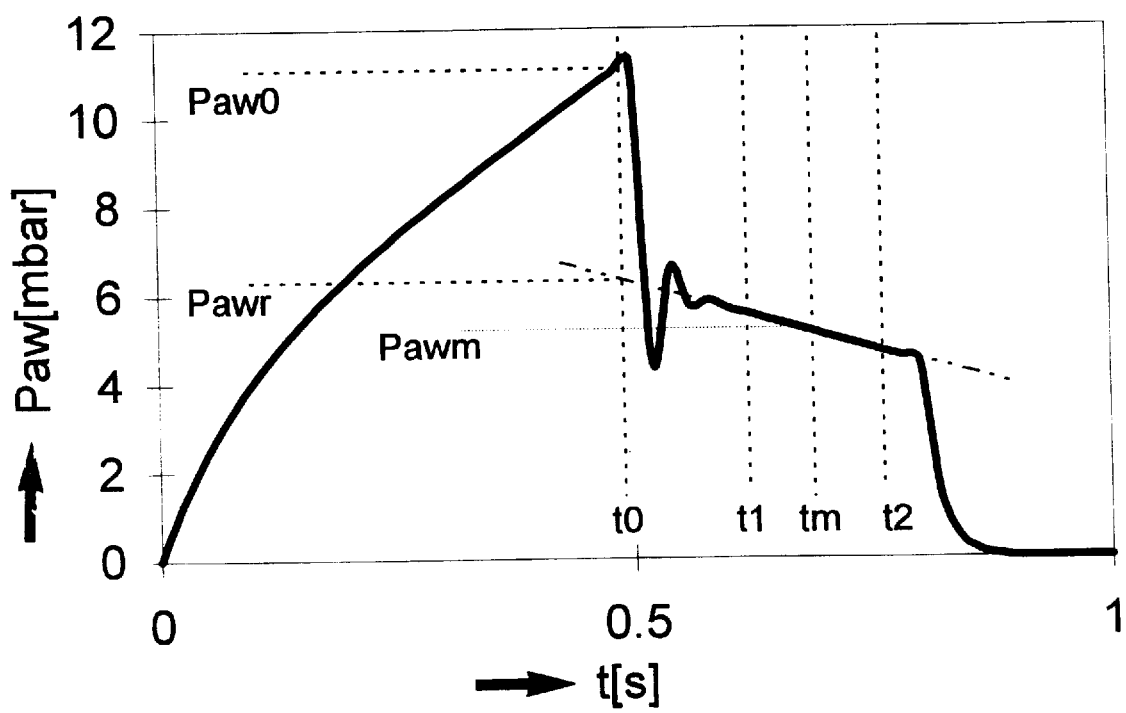
FIG. 2 shows the course over time of the airway pressure during an occlusion.

The airway pressure $P_{aw}$ is plotted over the time t for an inspiration phase in FIG. 2. An occlusion is initiated at the point in time $t_0$ at the airway pressure $P_{aw0}$. The airway pressure will then drop rapidly, and small vibrations will appear in the respiratory system, which will have subsided by the time $t_1$. The airway pressure $P_{aw}$ is measured several times during a measurement time between the points in time $t_1$ and $t_2$. By fitting a straight line to the measured values, a value is determined in the evaluating unit 11 for $dP_{aw}/dt$, and this value is assigned to the point in time $t_M$. The airway pressure $P_{awm}$ is present at the point in time $t_M$. By re-extrapolating the fitted straight line to the point in time $t_0$, a value $P_{awr}$ is obtained, which represents the airway pressure immediately after the beginning of the occlusion. The value of the resistance R can be determined according to Formula (7) from the values $P_{aw0}$ and $P_{awr}$ as well as the respiratory flow at the time $t_0$.

Figure 3:
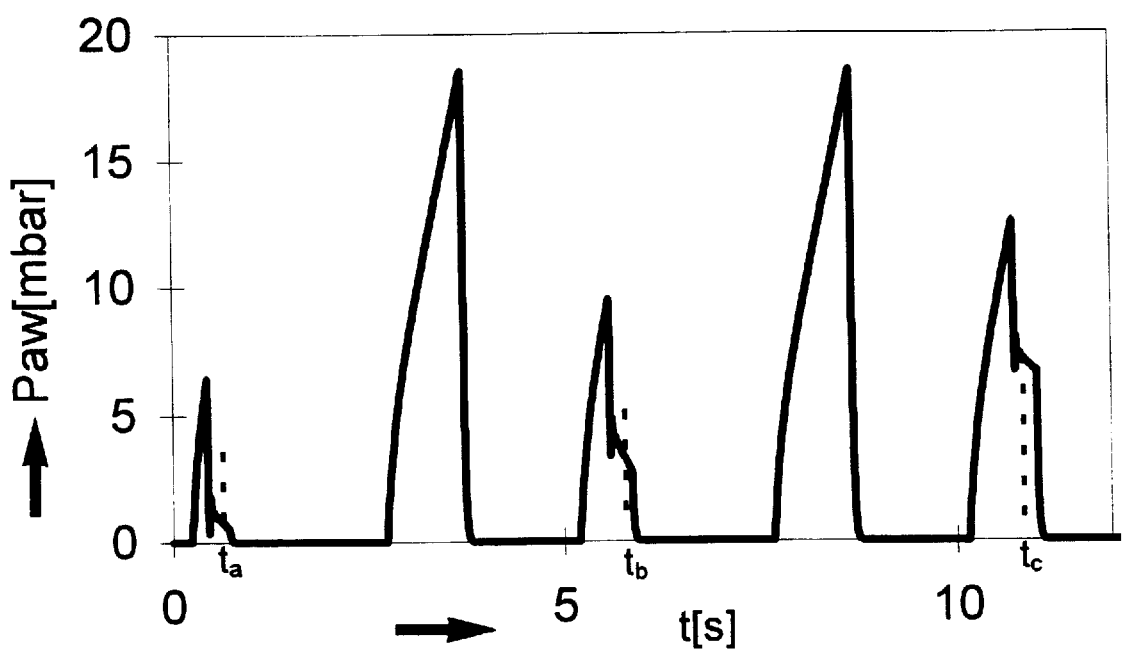
FIG. 3 shows the course over time of the airway pressure over a plurality of breaths.

As is shown in FIG. 3, the occlusion with the detection and evaluation of the measured values is repeated during a plurality of breaths at different points in time $t_a$, $t_b$, $t_c$ within the respective breaths.

Figure 4:
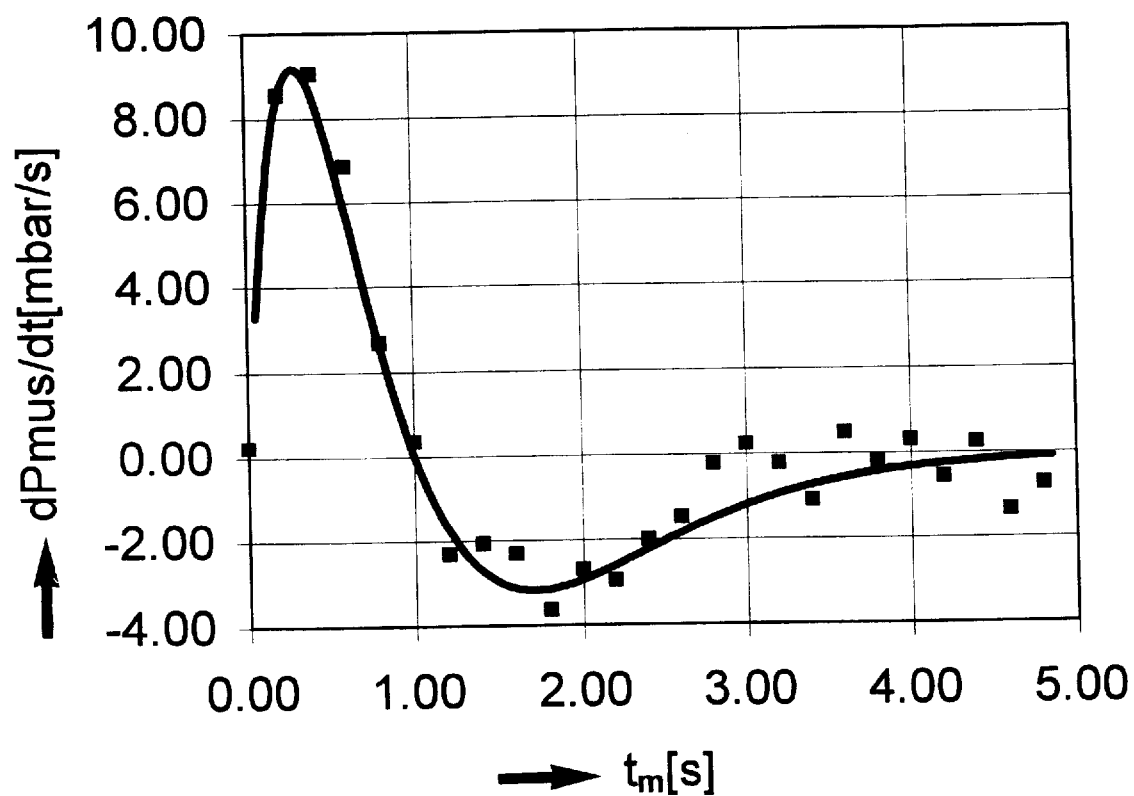
FIG. 4 shows the course over time of the change in the airway pressure.

FIG. 4 shows the measured values for $dP_{mus}/dt$ plotted over the measurement time $t_M$, wherein $t_M$ is related to one breathing cycle. The measured values are connected by a curve. In the areas in which the curve has a nearly linear course, the measurement points may be located relatively far apart and be connected by a straight line, without any appreciable errors occurring as a result in the evaluation. The measurement points must be spaced more closely to one another in the areas in which the curve is greatly curved.

Figure 5:
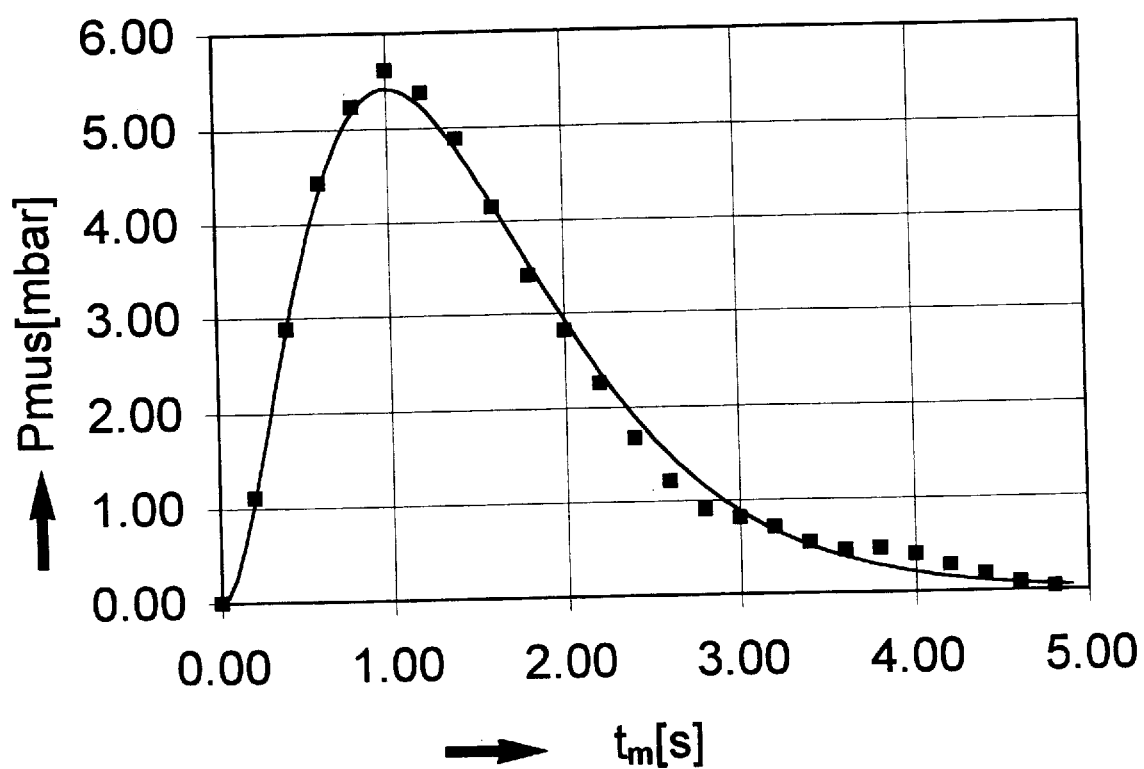
FIG. 5 shows the course over time of the muscle pressure.

FIG. 5 shows the integral of the curve in FIG. 4, which shows the course over time of the muscle pressure $P_{mus}$, with the exception of an additive constant K.

Figure 6:
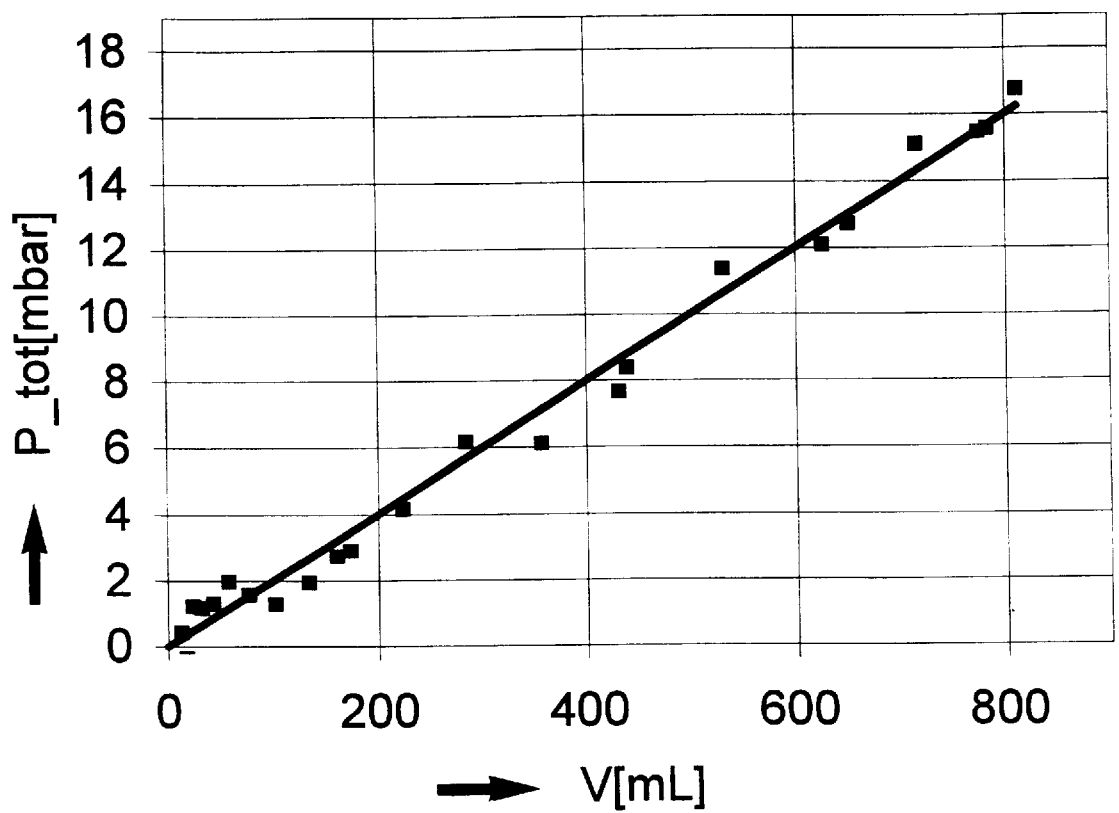
FIG. 6 shows the total pressure plotted over the tidal volume.

The value $P_{tot}$, which is obtained by the addition of the values of $P_{awm}$ (see FIG. 2) and $P_{mus}$ that belong to each other, is plotted over the volume V in FIG. 6. The volume V is always the volume that was inhaled or exhaled until the beginning of the occlusion. The slope of a straight line fitted to the measured values furnishes the compliance C of the patient's lungs (slope of the straight line 32 1/C).

Figure 7:
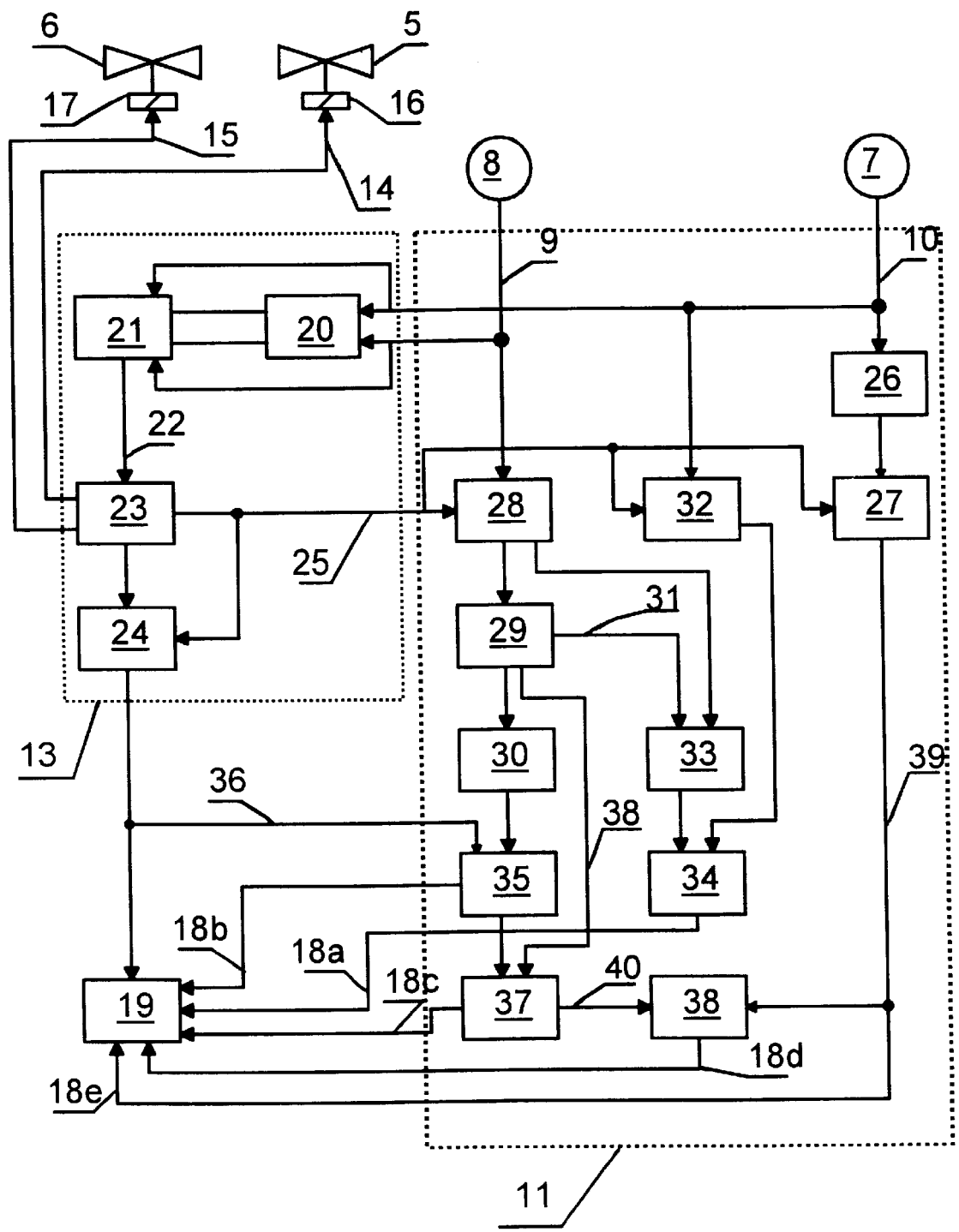
FIG. 7 shows a block diagram of the control and of the evaluating unit.

FIG. 7 shows a schematic block diagram of the evaluating unit 11 and of the control unit 13. The line 12 shown in FIG. 1 between the evaluating unit 11 and the control unit 13 is represented in greater detail as lines 9, 10, 25 and 36 in FIG. 7. The functions will be explained below:

Before the beginning of a measurement proper, a reference breath is stored in a memory 20 from the measured values arriving from the flow sensor 7 and the pressure sensor 8 via the lines 9 and 10. The measured values are continuously compared with the reference breath by means of a comparator 21 during the measurement. If the deviation between the measured values and the reference breath is below a presettable limit value, the breath is taken into account for the evaluation. The comparator 21 will then send a signal via a line 22 to an occlusion control unit 23, which closes the inspiration valve 5 and the expiration valve 6 by means of the actuators 16 and 17 via the lines 14 and 15.

The point in time relative to the beginning of the corresponding breath is stored in a memory 24. The storage is triggered by the occlusion control unit 23 via a line 25.

The measured values of the flow sensor 7 are integrated over time into the value of the volume V by means of an integrator 26. The value of the total volume inhaled or exhaled at the beginning of an occlusion is stored in a memory 27. The storage is initiated by the occlusion control unit 23 via the line 25.

The value $P_{aw0}$ of the airway pressure at the beginning of the occlusion, which is furnished by the pressure sensor 8, is stored in a memory 28. The change occurring over time in the airway pressure, which will be stored in a memory 30, is determined by a straight line fitting unit 29. The straight line fitting unit 29 furnishes the value $P_{awr}$ of the airway pressure, which is re-extrapolated to the point in time $t_0$, via a line 31.

The respiratory flow present at the point in time $t_0$ at the beginning of the occlusion is stored in a memory 32. The difference between $P_{aw0}$ and $P_{awr}$ is formed in a subtracting unit 33. This difference is divided in a divider 34 by the value of the respiratory flow being stored in the memory 32. The result is the resistance R; it is sent to the output device 19 via an output line 18a.

The change occurring over time in the airway pressure during the measurement time from $t_1$ to $t_2$ (see FIG. 2) is stored in the memory 30. The values for a plurality of breaths from the memory 30 are integrated in an integrator 35 over the measurement time, which arrives via a line 36 from the memory 24. The result is the muscle pressure $P_{mus}$; it is sent to the output device 19 via an output line 18b.

The muscle pressure $P_{mus}$ is added in an adder 37 to the value of $P_{awm}$, which arrives from the straight line fitting unit 29 via a line 38, to form the total pressure $P_{tot}$. The value of $P_{tot}$ is sent to the output device 19 via an output line 18c.

In a second straight line fitting unit 38, a straight line is fitted to the values of $P_{tot}$ which are plotted above the values of the volume V arriving from the memory 27 via a line 39 and arrive from the adder 37 via a line 40. The result is the compliance C; it is sent to the output device 19 via an output line 18d.

The values of the volume V from the memory 27 are sent to the output device 19 via an output line 18e, and the values of the measurement time are sent from the memory 24 to the output device 19 via the line 36. Thus, all the values needed are available for display here.

The circuits shown in FIG. 7 may be embodied as software as a computer program, or they may be designed as hardware in the form of analog calculation circuits.

While specific embodiments of the invention have been shown and described in detail to illustrate the application of the principles of the invention, it will be understood that the invention may be embodied otherwise without departing from such principles.

What is claimed is:

1. Process for determining mechanical properties of a respiratory system of a patient connected to a respiration device, the process comprising the steps of:

performing a plurality of occlusions of an airway of the patient during a plurality of breaths, each of said occlusions occurring in a separate one of said plurality of breaths, each of said occlusions also occurring at a different point in a respective one of said plurality of breaths;

determining respiratory flow and volume of the patient at a beginning of said each occlusion;

measuring airway pressure during said each occlusion;

determining a change occurring over time in said airway pressure during a measurement time within said each occlusion;

determining a change occurring over time in muscle pressure of the patient from said change in airway pressure.

2. A process in accordance with claim 1, wherein:

performing said occlusion of said airway during one of an inspiration phase and an expiration phase, a duration of said occlusion is short-term relative to one of said plurality of breaths;

said volume is one of inhaled and exhaled tidal volume;

said change in muscle pressure is determined for a plurality of points in a breathing cycle from measured and determined values;

muscle pressure is determined by integrating said change in muscle pressure, said integrating is performed over said breathing cycle to calculate a plurality of muscle pressures during said breathing cycle.

3. Process in accordance with claim 1, wherein:

muscle pressure is determined by integrating said change in muscle pressure, said integrating is performed over a breathing cycle to calculate a plurality of muscle pressures during said breathing cycle;

said muscle pressures are added to said measured airway pressures to form a total pressure;

said volume is one of inhaled and exhaled tidal volume;

a compliance of lungs of the patient is calculated from a derivation of values for said total pressure according to said tidal volume.

4. Process in accordance with claim 1, wherein:

a reference breath is determined for the patient;

said occlusion is triggered only when a particular breath is within a predetermined deviation from said reference breath.

5. Process in accordance with claim 3, wherein:

a reference breath is determined for the patient;

said occlusion is triggered only when a particular breath is within a predetermined deviation from said reference breath.

6. Process in accordance with claim 1, wherein:

a reference breath is determined for the patient;

evaluation of measured results is performed only when a particular breath is within a predetermined deviation from said reference breath.

7. Process in accordance with claim 1, wherein:

said volume is corrected by an effect due to one of a compliance and a resistance of the ventilator breathing system.

8. Device for determining mechanical properties of a respiratory system of a patient connected to a respiration device, the device comprising:

a control unit for bringing about a plurality of short-term occlusions of the patient's airways during one of an inspiration phase and/or an expiration phase of a plurality of breaths, each occlusion being in a separate one of said plurality of breaths, said control unit having means to initiate said occlusion at different points in time within each of said plurality of breaths;

a flow sensor for measuring respiratory flows, and one of inhaled or exhaled total volumes;

a pressure sensor for measuring airway pressures of the patient during said each of said plurality of breaths;

an evaluating unit for detecting a change occurring over time in said airway pressures during a measurement time of said each occlusion, said evaluating unit also determining a change occurring over time in muscle pressures of the patient from said respiratory flows, said total volumes and changes in said airway pressures.

9. A device in accordance with claim 8, wherein:

said evaluating unit calculates muscle pressures by integrating said change in muscle pressures;

said change in muscle pressures is determined for a plurality of points in a breathing cycle;

said integrating is performed over said breathing cycle to calculate a plurality of muscle pressures during said breathing cycle.

10. Device in accordance with claim 8, wherein:

said evaluating unit calculates muscle pressures by integrating said change in muscle pressures;

said integrating of said evaluating unit is performed over a breathing cycle to calculate a plurality of muscle pressures during said breathing cycle, said evaluating unit has means to add said muscle pressures to said airway pressures to form total pressures and to calculate a compliance of the patient's lungs from said total pressures according to said tidal volumes.

11. Device in accordance with claim 8, wherein:

said control unit has means for storing a representation of preceding breaths of the patient and to initiate said each occlusion only if a particular breath is substantially identical to said preceding breaths.

12. Device in accordance with claim 8, wherein:

said evaluating unit has means for storing a representation of preceding breaths of the patient and to evaluate measured values only if a particular breath is substantially identical to said preceding breaths.

13. Device in accordance with claim 8, wherein:

said evaluating unit has means to correct said volumes by an effect due to one of compliance and resistance of the ventilator breathing system.

14. Device in accordance with claim 8, wherein:

said flow and pressure sensors are arranged at a patient connection of the respirator.

15. Device in accordance with claim 8, wherein:

said sensors are part of the respirator.

16. Device for determining mechanical properties of a respiratory system of a patient connected to a respiration device, the device comprising:

a control unit for bringing about a plurality of short-term occlusions of the patient's airways during one of an inspiration phase and/or an expiration phase of a plurality of breaths, each occlusion being in a separate one of said plurality of breaths, said control unit having means to initiate said occlusion at different points in time within each of said plurality of breaths;

a flow sensor for measuring respiratory flows, and one of inhaled or exhaled total volumes;

a pressure sensor for measuring airway pressures of the patient during said each of said plurality of breaths;

an evaluating unit for detecting a change occurring over time in said airway pressures during a measurement time of said each occlusion, said evaluating unit also determining a change occurring over time in muscle pressures of the patient from said respiratory flows, said total volumes and changes in said airway pressures, said evaluating unit also calculating muscle pressures by integrating said change in muscle pressures.

17. A device in accordance with claim 16, wherein:

said change in muscle pressures is determined for a plurality of points in a breathing cycle;

said integrating is performed over said breathing cycle to calculate a plurality of muscle pressures during said breathing cycle.

18. Device in accordance with claim 16, wherein:

said integrating of said evaluating unit is performed over a breathing cycle to calculate a plurality of muscle pressures during said breathing cycle, said evaluating unit has means to add said muscle pressures to said airway pressures to form total pressures and to calculate a compliance of the patient's lungs from said total pressures according to said tidal volumes.

* * * * *